(12) United States Patent  (10) Patent No.: US 8,496,002 B2
Ellwanger et al.  (45) Date of Patent: Jul. 30, 2013

(54) POWDER INHALER DEVICES

(75) Inventors: Colleen Ellwanger, Lexington, MA (US); Brian Noble, Harvard, MA (US); Chuck Ganem, Cape Neddick, ME (US); Jake Ganem, Cape Neddick, ME (US); Kevin Stapleton, Seattle, WA (US)

(73) Assignee: Civitas Therapeutics, Inc., Chelsea, MA (US)

( * ) Notice: Subject to any disclaimer, the term of this patent is extended or adjusted under 35 U.S.C. 154(b) by 962 days.

(21) Appl. No.: 12/155,782

(22) Filed: Jun. 10, 2008

(65) Prior Publication Data
US 2009/0025721 A1    Jan. 29, 2009

Related U.S. Application Data

(60) Provisional application No. 60/929,092, filed on Jun. 12, 2007.

(51) Int. Cl.
A61M 15/00 (2006.01)
A61M 16/00 (2006.01)
B65D 83/06 (2006.01)
B05D 7/14 (2006.01)

(52) U.S. Cl.
USPC ................. 128/203.21; 128/203.15

(58) Field of Classification Search
USPC ............ 128/200.24, 203.15, 203.19, 203.21, 128/203.12, 203.23, 205.21, 200.12
See application file for complete search history.

(56) References Cited

U.S. PATENT DOCUMENTS

| | | |
|---|---|---|
| 3,518,992 A | 7/1970 | Colling et al. |
| 3,635,219 A | 1/1972 | Altounyan et al. |
| 3,669,113 A | 6/1972 | Altounyan et al. |
| 3,795,244 A | 3/1974 | Lax et al. |

(Continued)

FOREIGN PATENT DOCUMENTS

| | | |
|---|---|---|
| CA | 2020425 A1 | 1/1991 |
| EP | 0 407 276 A2 | 1/1991 |

(Continued)

OTHER PUBLICATIONS

Bisgaard, et al., "Fine particle mass from the diskus inhaler and turbuhaler inhaler in children with asthma," European Respiratory Journal, 11: 1111-1115 (May 1998).

(Continued)

*Primary Examiner* — Kristen Matter
*Assistant Examiner* — Peter S Vasat
(74) *Attorney, Agent, or Firm* — Carolyn S. Elmore, Esq.; Darlene A. Vanstone, Esq.; Elmore Patent Law Group, P.C.

(57) ABSTRACT

An improved inhalation device is provided for facilitating inhalation by a patient of powder medicaments contained in a receptacle. The inhalation device includes a staple assembly comprising a plunger and staple that are securely and robustly coupled to one another. Embodiments of the inhalation device have a cap that prevents or reduces the amount of dust and grime entering into the device. The cap is additionally configured to prevent or reduce inadvertent and unintentional operation of the device. The body portion and first casing portion of certain embodiments of the inhalation device are sealably coupled, restricting or reducing undesirable flow pathways that have an adverse effect on the operation of the device.

4 Claims, 11 Drawing Sheets

U.S. PATENT DOCUMENTS

| | | |
|---|---|---|
| 3,837,341 A | 9/1974 | Bell |
| 3,888,253 A | 6/1975 | Watt et al. |
| 3,906,950 A | 9/1975 | Cocozza |
| 3,991,761 A * | 11/1976 | Cocozza .................. 128/203.15 |
| 4,013,075 A | 3/1977 | Cocozza |
| 4,069,228 A | 1/1978 | Schellhammer et al. |
| 4,069,819 A | 1/1978 | Valentini et al. |
| 4,105,027 A | 8/1978 | Lundquist |
| 4,192,309 A | 3/1980 | Poulsen |
| 4,240,418 A | 12/1980 | Rosskamp et al. |
| 4,338,931 A | 7/1982 | Cavazza |
| 4,841,964 A | 6/1989 | Hurka et al. |
| 4,846,168 A | 7/1989 | Abiko et al. |
| 4,860,740 A | 8/1989 | Kirk et al. |
| 4,889,114 A | 12/1989 | Kladders |
| 4,995,285 A | 2/1991 | Hayakawa et al. |
| 4,995,385 A | 2/1991 | Valentini et al. |
| 5,042,472 A | 8/1991 | Bunin |
| 5,152,284 A | 10/1992 | Valentini et al. |
| 5,239,991 A | 8/1993 | Chawla et al. |
| 5,239,992 A | 8/1993 | Bougamont et al. |
| 5,301,666 A | 4/1994 | Lerk et al. |
| 5,349,947 A | 9/1994 | Newhouse et al. |
| 5,379,763 A | 1/1995 | Martin |
| 5,437,271 A | 8/1995 | Hodson et al. |
| 5,458,135 A | 10/1995 | Patton et al. |
| 5,507,281 A | 4/1996 | Kuhnel et al. |
| 5,524,613 A | 6/1996 | Haber et al. |
| 5,533,505 A | 7/1996 | Kallstrand et al. |
| 5,575,280 A | 11/1996 | Gupte et al. |
| 5,595,175 A | 1/1997 | Malcher et al. |
| 5,617,845 A | 4/1997 | Poss et al. |
| 5,647,349 A | 7/1997 | Ohki et al. |
| 5,651,359 A | 7/1997 | Bougamont et al. |
| 5,660,169 A | 8/1997 | Kallstrand et al. |
| 5,673,686 A | 10/1997 | Villax et al. |
| 5,685,294 A | 11/1997 | Gupte et al. |
| 5,699,789 A | 12/1997 | Hendricks |
| 5,727,546 A | 3/1998 | Clarke et al. |
| 5,740,794 A | 4/1998 | Smith et al. |
| 5,785,049 A | 7/1998 | Smith et al. |
| 5,787,881 A | 8/1998 | Chawla et al. |
| 5,797,391 A | 8/1998 | Cook et al. |
| 5,810,004 A | 9/1998 | Ohki et al. |
| 5,829,434 A | 11/1998 | Ambrosio et al. |
| 5,860,419 A | 1/1999 | Davies et al. |
| 5,896,855 A | 4/1999 | Hobbs et al. |
| 5,918,594 A | 7/1999 | Asking et al. |
| 5,921,237 A | 7/1999 | Eisele et al. |
| 6,065,472 A | 5/2000 | Anderson et al. |
| 6,089,228 A | 7/2000 | Smith et al. |
| 6,092,522 A | 7/2000 | Calvert et al. |
| 6,098,619 A | 8/2000 | Britto et al. |
| 6,102,035 A | 8/2000 | Asking et al. |
| 6,105,574 A | 8/2000 | Jahnsson et al. |
| 6,116,237 A | 9/2000 | Schultz et al. |
| 6,116,238 A | 9/2000 | Jackson et al. |
| 6,119,853 A | 9/2000 | Garrill et al. |
| 6,142,145 A | 11/2000 | Dagsland et al. |
| 6,187,269 B1 | 2/2001 | Lancesseur et al. |
| 6,237,590 B1 | 5/2001 | Leedom et al. |
| 6,273,085 B1 | 8/2001 | Eisele et al. |
| 6,286,507 B1 | 9/2001 | Jahnsson et al. |
| 6,332,461 B1 | 12/2001 | Hyppola et al. |
| 6,390,291 B1 | 5/2002 | Garrill et al. |
| 6,575,160 B1 | 6/2003 | Volgyesi |
| 6,615,826 B1 | 9/2003 | Gabrio et al. |
| 6,705,313 B2 | 3/2004 | Niccolai et al. |
| 6,732,732 B2 | 5/2004 | Edwards et al. |
| 6,766,799 B2 | 7/2004 | Edwards et al. |
| 7,146,978 B2 | 12/2006 | Edwards et al. |
| 7,278,425 B2 | 10/2007 | Edwards et al. |
| 2003/0094173 A1 | 5/2003 | Burr et al. |
| 2003/0131847 A1* | 7/2003 | Niccolai .................. 128/203.15 |
| 2003/0150453 A1* | 8/2003 | Edwards et al. ......... 128/203.21 |
| 2004/0154619 A1 | 8/2004 | Edwards et al. |
| 2005/0022812 A1 | 2/2005 | Hrkach |
| 2005/0051166 A1 | 3/2005 | Glusker et al. |
| 2005/0150492 A1* | 7/2005 | Dunkley et al. .......... 128/203.21 |
| 2006/0283448 A1 | 12/2006 | Edwards et al. |

FOREIGN PATENT DOCUMENTS

| | | |
|---|---|---|
| EP | 0 506 292 A1 | 9/1992 |
| EP | 1 062 962 A1 | 12/2000 |
| WO | WO-94/08552 A2 | 4/1994 |
| WO | WO-00/64519 A1 | 11/2000 |
| WO | WO-01/07107 A2 | 2/2001 |
| WO | WO-2004/091707 A2 | 10/2004 |

OTHER PUBLICATIONS de Boer, et al., "Inhalation characteristics and their effects on in vitro drug delivery from dry powder inhalers, Part 1. Inhalation characteristics, work of breathing and volunteers' preference in dependence of the inhaler resistance," International Journal of Pharmaceutics 130: 231-244 (1996).

Dunbar, et al., "A comparison of dry powder inhaler dose delivery characteristics using a power criterion," PDA Journal of Pharmaceutical Science & Technology, 54(6): 478-484, (Nov./Dec. 2000).

Feddah, et al., "In-vitro characterisation of metered dose inhaler versus dry powder inhaler glucocorticoid products: Influence of inspiratory flow rates," J. Pham. Pharmaceut. Sci. (www.ualberta.ca/-csps), 3(3): 317-324 (2000).

Koskela, et al., "Efficacy of salbutamol via Easyhaler® unaffected by low inspiratory flow," Respiratory Medicine 94(12): 1229-1233 (Dec. 2000).

Nielsen, et al., "Flow-dependent effect of formoterol dry-powder inhaled from the aerolizer®," European Respiratory Journal, 10: 2105-2109 (Sep. 1997).

Richards and Saunders, "Need for a comparative performance standard for dry powder inhalers," Thorax 48: 1186-1187 (Nov. 1993).

Ross and Schultz, "Effect of inhalation flow rate on the dosing characteristics of dry powder inhaler (DPI) and metered dose inhaler (MDI) products," Journal of Aerosol Medicine, 9(2): 215-226 (1996).

Smith, et al., "Influence of flow rate on aerosol particle size distributions from pressurized and breath-actuated inhalers," Journal of Aerosol Medicine, 11(4): 231-245 (1998).

* cited by examiner

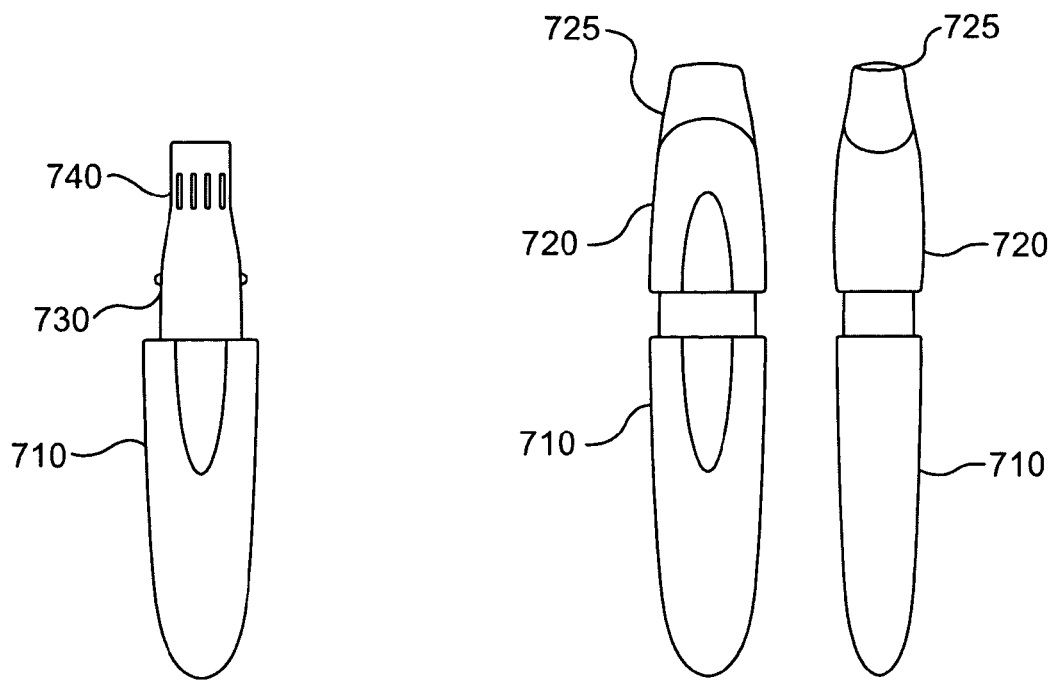
FIG. 7A   FIG. 7B
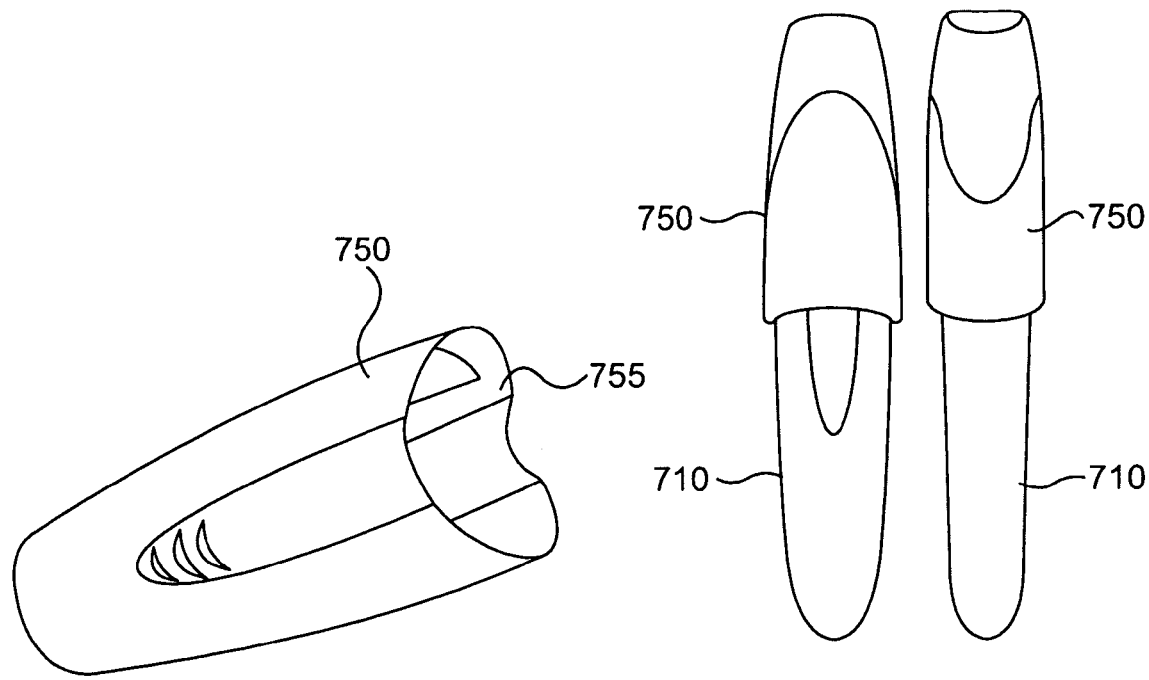
FIG. 7C   FIG. 7D

POWDER INHALER DEVICES

BACKGROUND OF THE INVENTION

1. Field of the Invention

The present invention relates generally to facilitating release of powder contained in a receptacle. More specifically, the present invention relates to the administration of medication by a method and apparatus for facilitating inhalation of powder medicaments.

2. Related Art

In the medical field, it is often desirable to administer various forms of medication to patients. Well known methods of introducing medication into the human body include the oral ingestion of capsules and tablets, intravenous injection through hypodermic needles, and numerous others. In one method, certain medications may be inhaled into a patient's respiratory tract and lungs through the nose or mouth. Certain of these medications, such as bronchodilators, corticosteroids, etc., for the treatment of asthma and other respiratory anomalies, may be aimed at the respiratory tract directly. Others are inhaled for purposes of systemic treatment, i.e. for treatment of any area of the body through absorption from the respiratory tract through the lung tissue, into the deep lungs, and into the bloodstream. Each of these medications comes in a variety of forms, including fluids, which are commonly administered as an aerosol vapor or mist, as well as solids. Inhalable solids typically take the form of fine, dry powders. Specialized devices, such as inhalers, are provided to assist the patient in directing these fine powder medications into the respiratory tract.

Various types of inhalers are known for the administration of dry powder medicaments. However, each of these inhalers suffers certain drawbacks. For example, U.S. Pat. No. 5,787,881 discloses an inhaler that is used with encapsulated dry powder medicaments. However, use of this device requires numerous steps and imposes a number of inconveniences on a user. For example, the medication capsules used with the device have an aperture formed therein prior to insertion into an opening in the inhaler. Therefore, there exists a danger that an amount of medication may be lost prior to or during insertion into the device. After insertion of the capsule, use of the device requires the additional step that a cover must be closed before the medication may be inhaled.

Inhalation devices configured for use with a capsule containing some type of medicament are shown in U.S. Pat. No. 4,069,819 to Valentini et al. ("the '819 patent") and U.S. Pat. No. 4,995,385 to Valentini et al. ("the '385 patent"). The inhalation device described in the '385 patent was developed to overcome the drawbacks of the device described in the '819 patent. Particularly, in a large number of cases, the device described in the '819 patent experienced irregular and incomplete emptying of the capsule, thereby resulting in difficulties in properly administering the medicament in the capsule. The inhalation device described in the '385 patent attempts to overcome this deficiency by tapering the nebulization chamber toward the end surface that comprises the discharge holes. Thus, the nebulization chamber of the '385 patent is not cylindrical, but rather frusto-conical in form in an attempt to achieve regular complete emptying of the nebulization chamber.

However, further improvements in the design of inhalation devices are needed to achieve high emitted doses and highly dispersed powders while maintaining low resistance, especially when the inhaler is used with high doses and is operated at low peak inspiratory flow rates (PIFR) and low inhalation volumes. As used herein, "emitted dose" (ED) refers to the percentage of the dose of powder medicament that is emitted from a receptacle in the inhalation device. The dispersal of the powder can be quantified by measuring the volume mean geometric diameter (VMGD) of the emitted powder. As used herein "volume mean geometric diameter" refers to the average geometric diameter of the powder. As used herein, "resistance" refers to the square root of the pressure gradient across the inhaler divided by the peak inspiratory flow rate through the inhaler. As used herein "low peak inspiratory flow rate" refers to a peak inspiratory flow rate of approximately 25 L/min or less. Moreover, improvements are needed to achieve high emitted doses and highly dispersed powders that are consistently reproducible, i.e., that have a low standard deviation of emitted dose percentage and VMGD, respectively.

U.S. Pat. Nos. 6,766,799 and 6,732,732, which are assigned to the same entity as the one to which the current application is under an obligation of assignment, disclose further improvements over previously known devices. These patents disclose, among other things, a ring that is circumferentially coupled to the inside of a chamber for receiving the medicament capsule. Such a ring is intended to improve the reproducibility of the emitted dose during operation of the device. The patents also disclose staples of differing configurations for puncturing the receptacle during operation of the device.

Another drawback of the inhalation devices described in the '819 and the '385 patents is the piercing device that is used to puncture the capsule. Such conventional piercing devices are formed from circular stock, with the points created by pinching the stock at an angle, thereby creating a single sharp cutting edge. Drawbacks of such a design are that the point (which must puncture the capsule material) is often rounded, lessening its effectiveness as a piercing device. Moreover, burrs often form on the lower edge, which can stop the piercing device from retracting from the capsule, thereby causing a device failure. The holes formed by such a conventional piercing device are generally round, and do not have the appearance of being cut by a sharp edge. With such a conventional design, the capsule is often crushed, rather than punctured or pierced. If such a conventional piercing device is used with brittle capsule materials such as gelatin, pieces of capsule material of a size that can be inhaled are usually broken off from the capsule. Thus, conventional piercing devices are less than optimal, particularly for brittle capsule material.

The co-owned '799 and '732 patents additionally disclose staples of differing configurations and prongs for puncturing the receptacle during operation of the device. These configurations are intended to improve the operation of the inhalation device. These patents also disclose means for indicating when the powder in the inhaler is ready for inhalation by the user, which is a useful improvement over devices previously known before the '799 and '732 patents.

There is a need, however, for further improvements of such inhalation devices. Namely, there is a need for reliable attachment of the staple for puncturing the capsule or receptacle to the rest of the device, considering the repetitive use and forceful impacts that the staple-device attachment undergoes during operation. In addition, there is a need to reduce or eliminate the possibility of external dust and grime from entering and adversely affecting the operation of the device during periods of non-use, as well as periods of use. Additionally, there is a need to prevent inadvertent and unintentional operation of the device, which might occur when components of the device are subjected to random forces that trigger its operation without the volition of the user. Finally, there is a need for reducing undesired air flow into the inhaler device at its rest position, which has an adverse impact on the effectiveness of the device.

Thus, there is a need in the art for an improved method and apparatus for facilitating inhalation of dry powder medicaments. What is needed is an inhaler that provides for reliable and robust attachment of the staple, that prevents dust and grime from entering into the device and prevents unintentional operation of the device, and that reduces undesired air flow in to the inhaler device at its rest position.

SUMMARY OF THE INVENTION

In one embodiment of the invention, an inhalation device for administering a dose of powder contained in a receptacle is provided. The inhalation device includes a first casing portion and a second casing portion movably coupled to the first casing portion. The second casing portion includes a mouthpiece portion and a chamber configured to hold the receptacle. A plunger is coupled to the first casing portion, movably coupled to the second casing portion, and additionally includes a notched end. The inhaler device includes a hook member that is coupled to the plunger in a manner that secures a substantially U-shaped staple to the plunger.

In another embodiment of the invention, the plunger of the inhalation device has a substantially flat surface and includes at least one projecting portion that projects from the flat surface. The at least one projecting portion swagingly secures a U-shaped staple to the plunger.

In yet another embodiment of the invention, the base of the staple of the inhaler device has a thick cross section relative to the tines of the staple. One of the base and the plunger has at least one flange, and the other has at least one corresponding projecting hook which is configured to receive the at least one flange.

In yet another embodiment of the invention, at least one tine is secured to the distal end of the plunger by injection molding the at least one tine in a volume of space within the distal end of the plunger.

Another embodiment of the invention provides for sealable coupling of the first casing portion and the body portion of an inhalation device in a rest position of the inhalation device. In this embodiment, an end of one of the first casing portion and the body portion has a radially projecting portion around its circumference, and an end of the other of the two has a concave cross section. Further, the radially projecting portion has a convex cross section. The coupling of the concave and convex portions substantially provides a seal when the inhalation device is in its rest position.

Another embodiment of the invention also provides for sealable coupling of the first casing portion and the body portion of an inhalation device in a rest position of the inhalation device. In this embodiment, an insert element is receivably coupled to one of the first casing portion and the body portion. The insert element forms a closed curve substantially normal to an axis of substantial symmetry of at least one of the first casing portion and the body portion. The insert element is sealably coupled to both the first casing portion and the body portion in a rest position of the inhalation device.

Another embodiment of the invention provides a cap that encloses the second casing portion when the cap is engaged to the inhalation device, and additionally prevents the movement of the first casing portion of the inhalation device with respect to the second casing portion.

BRIEF DESCRIPTION OF THE FIGURES

The present invention is described with reference to the accompanying drawings. In the drawings, like reference numbers indicate identical or functionally similar elements.

FIG. 7A is a view of an inhaler without the mouthpiece portion attached.

FIG. 7B is two side views of the inhaler of FIG. 7A with the mouthpiece portion attached.

FIG. 7C is a view of a cap in accordance with an embodiment of the invention.

FIG. 7D is two side views of the cap of FIG. 7C secured to an inhaler device.

DETAILED DESCRIPTION OF THE PREFERRED EMBODIMENTS

Overview

Figure 1:
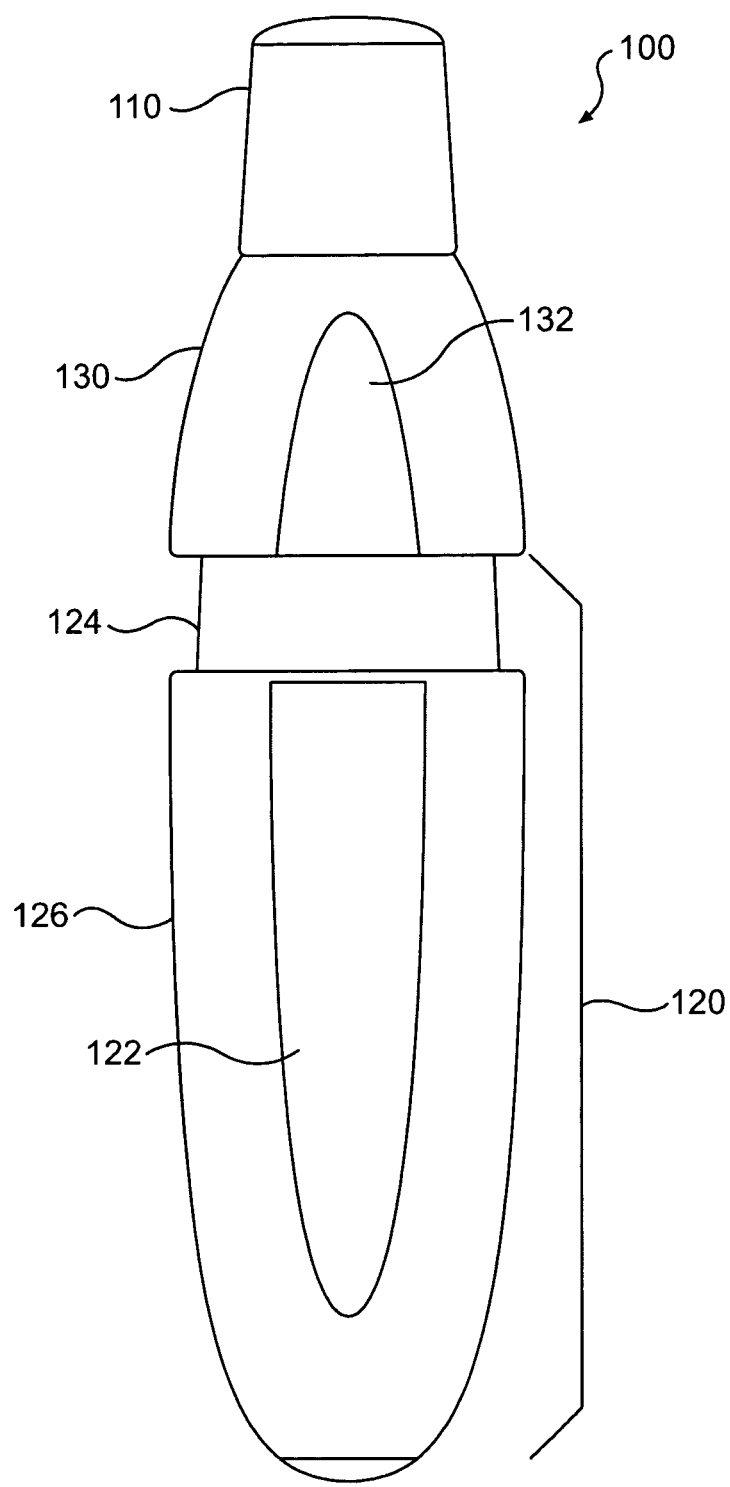
FIG. 1 is a front view of one embodiment of an inhaler device that may be used with embodiments of the present invention.

The present invention provides an improved method and apparatus for facilitating release of powder. In a preferred embodiment, the powder is contained in a receptacle. As used herein, the term "receptacle" includes but is not limited to, for example, a capsule, blister, film covered container well, chamber, and other suitable means of storing a powder known to those skilled in the art. The present invention will be described below in the context of a method and apparatus for dispensing dry powder medicaments for inhalation by a patient. However, it should be apparent to one skilled in the art that the invention is not limited to such an exemplary embodiment, and could be used for other purposes.

The methods of the present invention use an inhaler to dispense powder by inhalation. In embodiments of the invention, a user operates the device to puncture the receptacle to disperse powder in the chamber, and inhales the powder through the inhalation portion.

As used herein, "attachment" and "coupling" are intended to cover embodiments in which two pieces are removably or irremovably attached to one another, as well as embodiments in which the two pieces are fused or permanently attached to one another.

Inhaler and Associated Method of the Present Invention

A front view of one embodiment of an inhalation device 100 is shown in FIG. 1. The rear view of device 100 is substantially identical to the front view. Device 100 includes a first or lower casing portion 120 and a second or upper casing portion 130 removably coupled to first casing portion 120. Upper casing portion 130 and lower casing portion 120 include a flattened region 132 and 122, respectively, for ease of gripping the casing for use by a patient. Lower casing portion 120 preferably includes an outer casing 126 and an inner casing 124 movably received within outer casing 126. A removable cap 110 as shown in FIG. 1 may be provided at the user or inhalation end of the device.

Preferred materials for device 100 include Food and Drug Administration (FDA) approved, USP tested plastics. Preferably, device 100 is manufactured using an injection molding process, the details of which would be readily apparent to one skilled in the art.

FIG. 2 is a cross-section of device 100 taken along a plane that is parallel to the axis of substantial symmetry of device 100. As shown in FIG. 2, device 100 includes an inhalation or emitter portion 220. Inhalation portion 220 comprises a hemispheric region 222 that defines a plurality of apertures 224. It should be understood that the present invention is not limited to a particular number of apertures 224, and can be configured such that at least one aperture 224 is provided. An inhalation piece 226 is provided to allow for inhalation of the medicament by a user. Inhalation piece 226 can be configured as a mouth piece for inhalation through a user's mouth. Alternatively, inhalation piece 226 can be configured as a nose piece for inhalation through a user's nose. For purposes of this application, "mouthpiece" shall denote mouth pieces for inhalation through a user's mouth and nose pieces for inhalation through a user's nose, as well as other possibilities such as a piece for insertion in or on a tracheotomy tube in a patient undergoing, or who has had, a tracheotomy.

Device 100 includes a cylindrical chamber 210 that is defined by a straight wall 212 of circular cross-section. Chamber 210 has a proximal end 214 and a distal end 216. A plurality of vents 218 are defined by wall 212, and are configured for introducing air into chamber 210 to disperse powder released from a capsule 219. It should be understood that the present invention is not limited to a particular number of vents 218, and can be configured such that at least one vent 218 is provided. Powder released from capsule 219 is dispersed in chamber 210 and inhaled through apertures 224 and inhalation piece 226 by the user.

In other embodiments of the invention, receptacles other than capsules are used, such as blisters and film covered container wells as is known in the art. In one embodiment, the volume of the receptacle is at least about 0.37 $cm^3$. In another embodiment, the volume of the receptacle is at least about 0.48 $cm^3$. In yet another embodiment, the receptacles have a volume of at least about 0.67 $cm^3$ or 0.95 $cm^3$. In one embodiment of the invention, the receptacle is a capsule designated with a capsule size 2, 1, 0, 00, or 000. Suitable capsules can be obtained, for example, from Shionogi (Rockville, Md.). Blisters can be obtained, for example, from Hueck Foils, (Wall, N.J.).

The receptacle encloses or stores particles, also referred to herein as powders. The receptacle is filled with particles in a manner known to one skilled in the art. For example, vacuum filling or tamping technologies may be used. Generally, filling the receptacle with powder can be carried out by methods known in the art. In one embodiment of the invention, the particle or powder enclosed or stored in the receptacle have a mass of at least about 5 milligrams (mg). In another embodiment, the mass of the particles stored or enclosed in the receptacle is at least about 10 mg, and up to approximately 50 mg. In a preferred embodiment, the mass of the particles is approximately 20 mg.

In one embodiment of the present invention, particles used with the device have a tap density of less than about 0.4 g/$cm^3$. Particles having a tap density of less than about 0.4 g/$cm^3$ are referred to herein as "aerodynamically light". In a preferred embodiment, the particles have a tap density of near to or less than about 0.1 g/$cm^3$. Tap density is a measure of the envelope mass density characterizing a particle. The envelope mass density of particles of a statistically isotropic shape is defined as the mass of the particle divided by the minimum sphere envelope volume within which it can be enclosed. Features that can contribute to low tap density include irregular surface texture and hollow or porous structure. Particularly preferred particles and powders are described in U.S. Pat. Nos. 6,136,295, 5,985,309, 5,874,064, 5,855,913 and 6,858,199, filed Jun. 9, 2000 entitled "High Efficient Delivery of a Large Therapeutic Mass Aerosol", the entirety of each of the foregoing patents and patent applications is hereby incorporated herein by reference.

Device 100 includes a staple assembly 230 that is used to puncture capsule 219 to release powder contained therein into chamber 210. In the embodiment shown in FIG. 2, staple assembly 230 includes at one end a substantially U-shaped staple 232 that has two prongs. In this embodiment, each of the prongs of U-shaped staple 232 is configured with a square cross-section 234, thereby providing a sharp point and two cutting edges.

Previously known staple assemblies for puncturing a receptacle or capsule in inhaler devices include prongs (or tines) that have wide, broad surfaces that are intended as puncturing edges. Although such staple assemblies may be used with embodiments of the invention, more effective puncturing of the receptacle may be achieved using staple assemblies with prongs that have sharp points. Wide broad surfaces require greater force to puncture a rounded surface such as a capsule, causing the capsule to buckle in an undesirable way. Staple assemblies that have prongs with sharp points for puncturing, as disclosed, for example, in U.S. patent application Ser. No. 10/771,551, which is assigned to the same entity to which the present application is under an obligation of assignment, do not present such problems. For that reason, preferred embodiments of the invention, as disclosed below, utilize staple assemblies that have prongs with sharp puncturing points.

The inhaler of the present invention is preferably configured with a staple assembly for puncturing the receptacle that improves puncturing performance, particularly with brittle receptacle material. In one preferred embodiment, the staple assembly for puncturing the receptacle of the present invention includes as a substantially U-shaped staple that is attached to a plunger, with each of the two prongs of the U-shaped staple having a sharp point and two cutting edges. In one such embodiment, each prong has a square cross-section, with the staple material being bent around a face so that the innermost part of the U-shaped staple is flat. In another such embodiment, the staple material is rotated 45 degrees so that it is bent around an edge so that the innermost part of the U-shaped staple is an edge. In such an embodiment, the end surface of each prong is an angled diamond-shaped surface.

In another preferred embodiment, the staple assembly for puncturing the receptacle is configured as a substantially longitudinal prong that is attached to a plunger, with the prong comprising a puncturing surface on the distal end, a primary cutting surface running from the proximal end to the distal end of the prong and terminating at the puncturing surface, and a substantially planar face opposite to the primary cutting edge and running from the proximal end to the distal end of the prong. The prong preferably has an angled surface at the distal end, the angled surface having a distal end terminating at the puncturing surface and a proximal end terminating at the substantially planar face. In addition, the prong is preferably tapered so that the distal end is smaller than the proximal end, to facilitate removing the prong from a receptacle. The prong also preferably has a plurality of longitudinal faces and a plurality of longitudinal edges running from the proximal end to the distal end of the prong.

The prong is configured to create an opening in a wall by forming a hanging chad in the wall, the hanging chad having a free end formed by the puncturing surface and the primary cutting edge and a hinge coupled to the wall formed by the face. In a preferred embodiment, the prong is configured to open the hanging chad to an angle of at least 30 to 45 degrees between the minor axis of the receptacle and the hanging chad, wherein the minor axis is substantially perpendicular to a longitudinal axis of the receptacle, which is substantially parallel to the longitudinal prong.

Other embodiments of staple assemblies for puncturing a capsule are disclosed and discussed in U.S. Pat. Nos. 6,766, 799 and 6,732,732, which are herein incorporated by reference in their entirety.

Staple assembly 230 is preferably configured to be movable between a non-puncturing position (as depicted in FIG. 1) and a puncturing position. In the puncturing position, prongs 232 pierce or puncture capsule 219 to make holes therein. In a preferred embodiment, a means for biasing is provided that biases staple assembly 230 in the non-puncturing position. In the embodiment shown in FIG. 2, the means for biasing is configured as a spring 242 that biases the substantially U-shaped staple (and staple assembly 230 to which it is attached) in the non-puncturing position.

Figure 2:
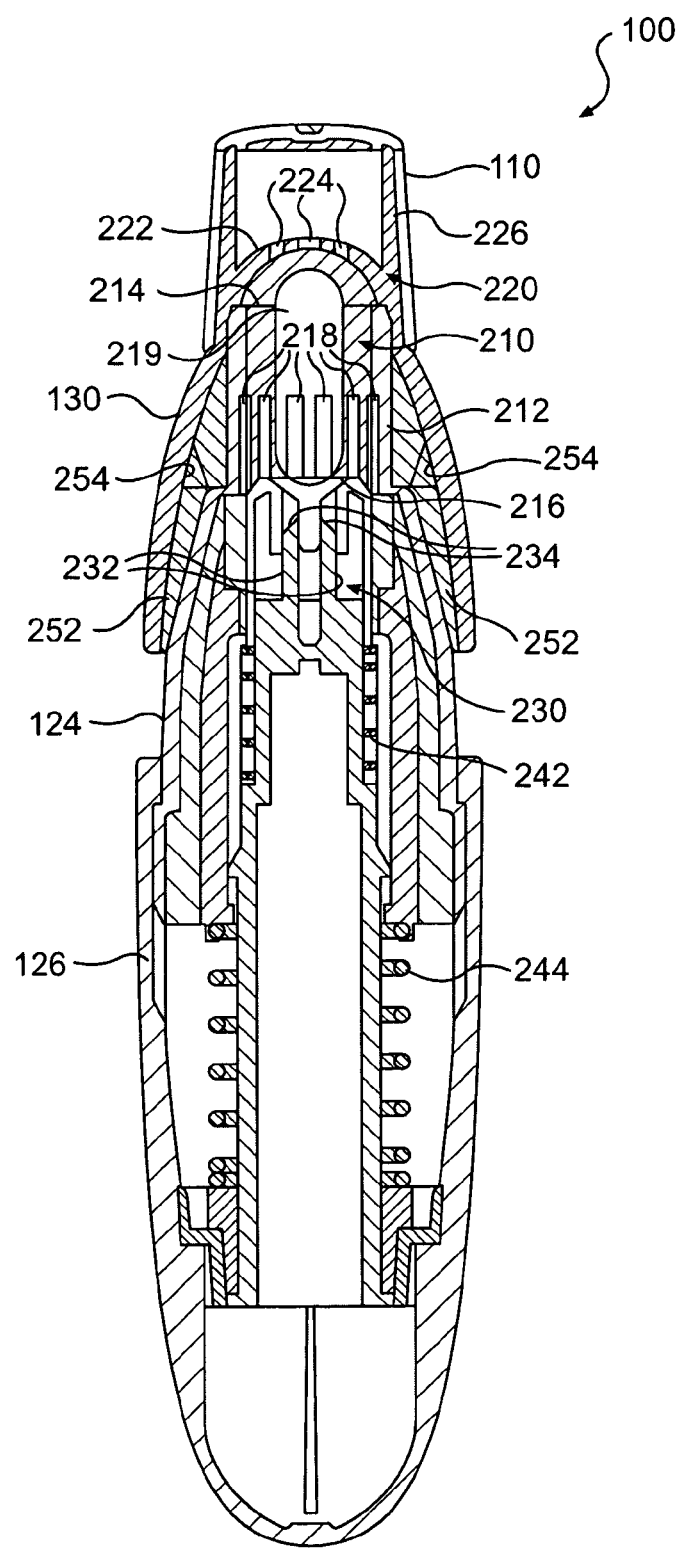
FIG. 2 is a cross-sectional view of the inhaler device of FIG. 1 taken along a plane parallel to an axis of substantial symmetry of the device.

As noted with respect to FIG. 1, device 100 includes inner casing 124 and outer casing 126. As shown in FIG. 2, a spring 244 is disposed in lower casing portion 120 that biases inner casing 124 in an outward position. Upon compression of spring 244, inner casing 124 moves from the outward position to an inward position, thereby drawing lower casing portion 120 toward upper casing portion 130. Compression of spring 244 also causes compression of spring 242, thereby causing staple assembly 230 to move to the puncturing position. Upon release of compression, springs 242 and 244 return to their biased state, thereby returning staple assembly 230 to its non-puncturing position, and inner casing 124 to its outward position.

A pair of flanges 252 is disposed on first casing portion 120. A pair of grooves 254 is disposed on second casing portion 130 so that flanges 252 can be received within grooves 254 to thereby couple the first and second casing portions. Preferably, the first and second casing portions are coupled with a friction-fit engagement. A friction-fit engagement can be achieved using the groove and flange arrangement depicted in FIG. 2. Other alternative configurations for a friction-fit engagement would be readily apparent to one skilled in the art.

Figure 3A:
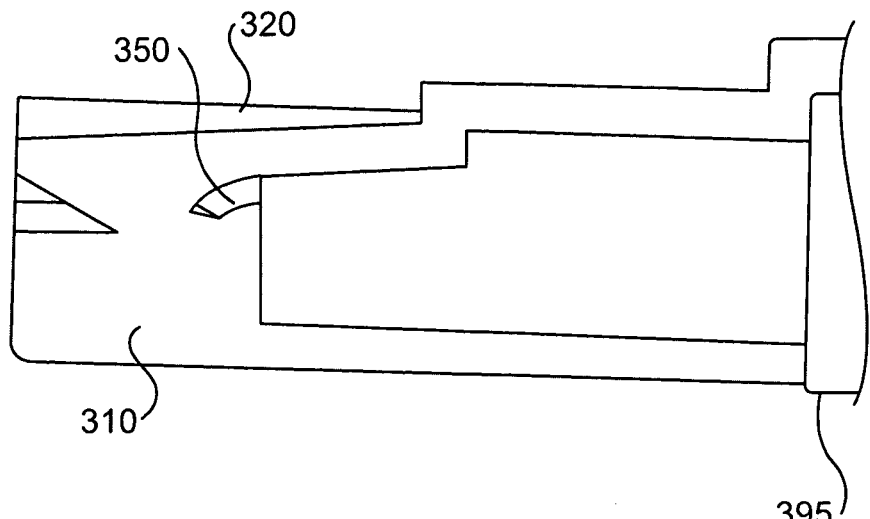
FIG. 3A is a side view of the distal end of a plunger in accordance with an embodiment of the invention.
Figure 3B:
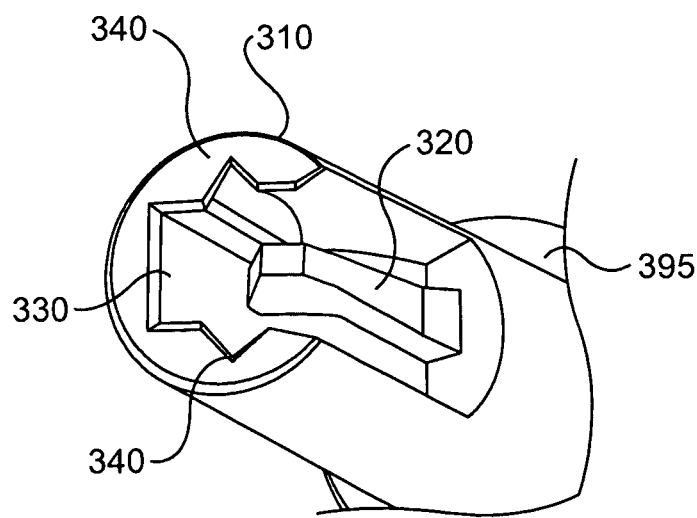
FIG. 3B is a view in perspective of the distal end of the plunger of FIG. 3A.
Figure 3C:
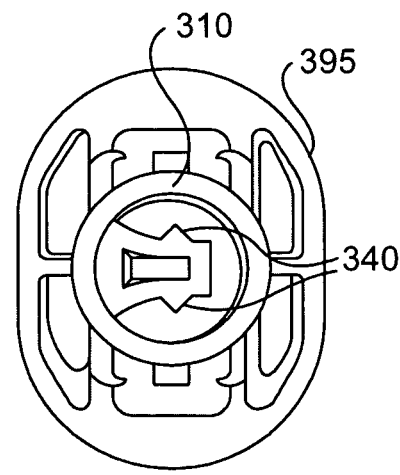
FIG. 3C is a top view of the distal end of the plunger of FIG. 3A.

In the inhaler of FIG. 2, staple 232 is one part of the single piece that is the staple assembly 230. In certain embodiments of the current invention, the staple assembly comprises at least two parts, a staple and a plunger, with the staple attached at the distal end of the plunger. FIGS. 3A, 3B and 3C show the distal end 310 of plunger 395 of staple assembly 230, in a first such embodiment of the present invention. The term "distal end", when used in reference to the plunger, denotes the end of the plunger that is furthest from the first casing portion (i.e., the end that is nearest the mouth or nose of the user when the device is in operation.) FIG. 3A illustrates distal end 310 of this embodiment in profile, with the line of sight substantially perpendicular to each of the axes of substantial symmetry of plunger 395 and distal end 310. FIG. 3B illustrates distal end 310 in perspective, from a line of sight forming an obtuse angle with these axes. FIG. 3C shows a view of distal end 310 looking down along the axes of plunger 395 and distal end 310. In this embodiment, distal end 310 is formed to contain notch 330, which provides the space in which the means for the staple attachment and the staple are situated. In this embodiment, hook 320, which is attached to distal end 310 and functions as the means for attaching a staple to distal end 310, is configured to fix a staple (not shown in FIG. 3 but similar, for example, to U-shaped staple 490 of FIG. 4B) to distal end 310 by compression of the staple between hook 320 and distal end 310. In the configuration in which the staple is attached to the distal end 310, the bottom of the U-part of the staple threads through slot 350, which is formed from a gap between hook 320 and distal end 310. In an aspect of this embodiment (shown in FIG. 3A), grooves 340, located substantially diametrically opposed from one another along a cross section of distal end 310, provide support for the sides of the U-shaped staple, which provides further compressive support in fixing the U-shaped staple to distal end 310. The staple and hook 320 may be fixed onto distal end 310 during manufacture of plunger 232 through, for example, injection molding, in a manner that will be apparent to those of skill in the art. In preferred embodiment, hook 320 is made from the same material as distal end 310, and is fused by injection molding onto it.

Figure 4A:
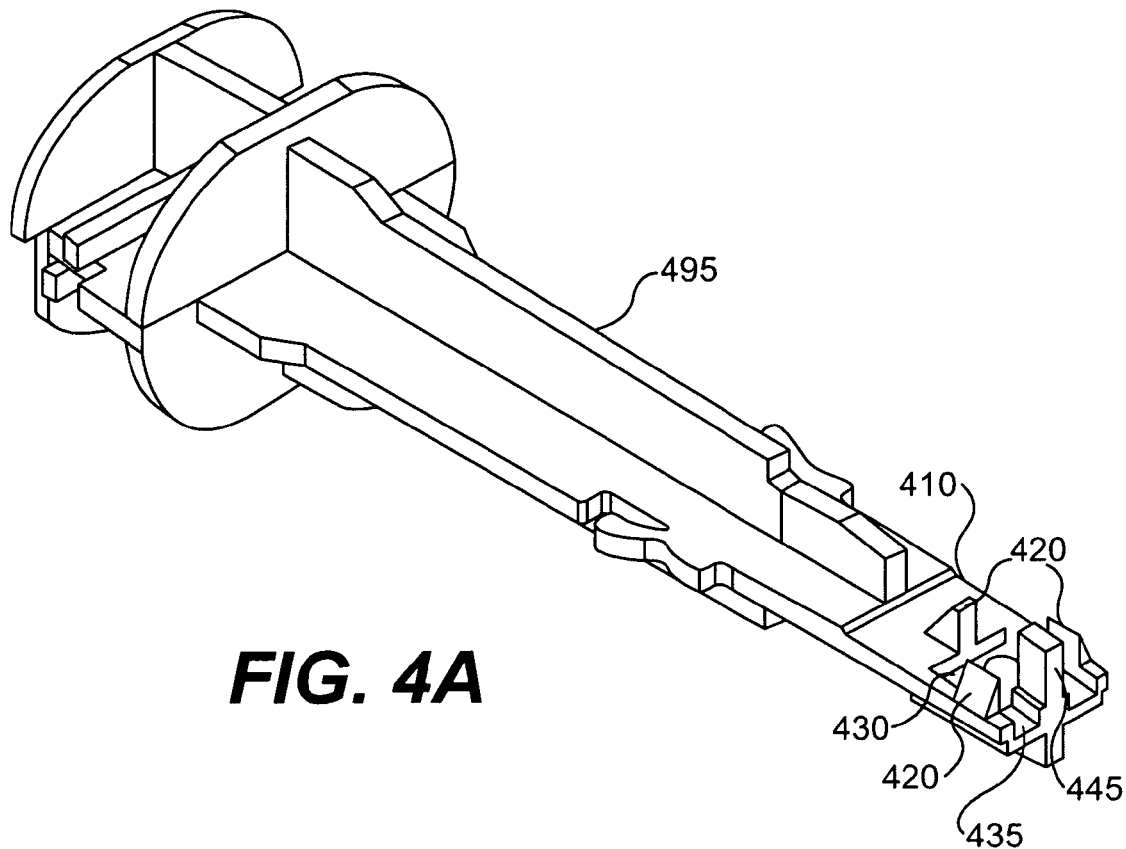
FIG. 4A is a view in perspective of a plunger in accordance with another embodiment of the invention.
Figure 4B:
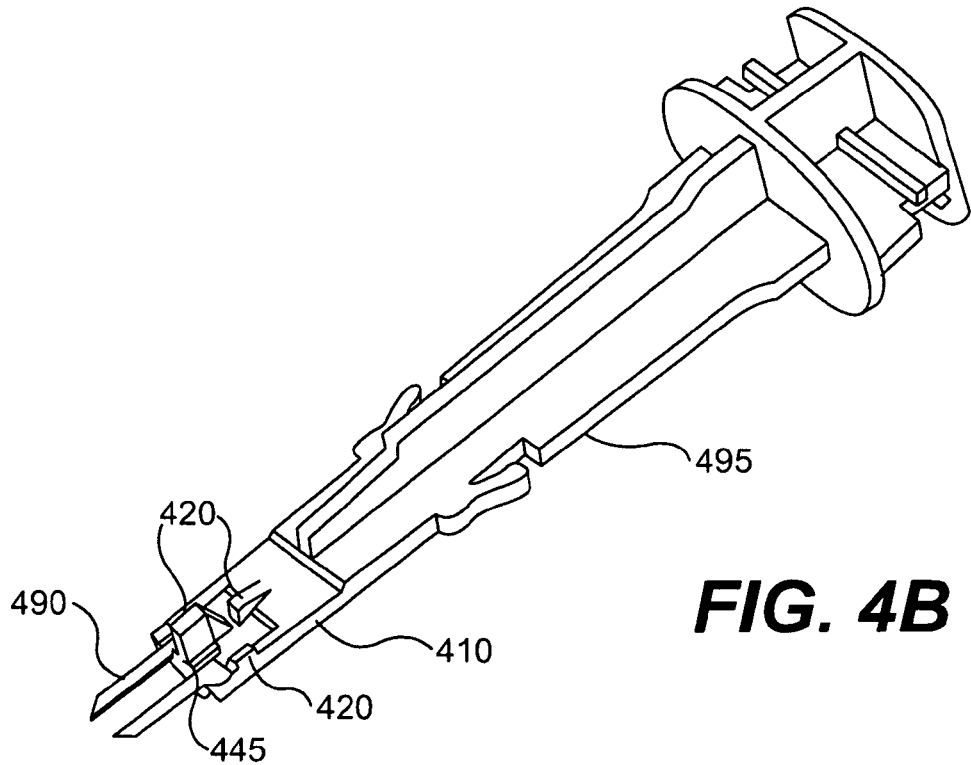
FIG. 4B is a view in perspective of the plunger in accordance with the embodiment of FIG. 4A in which a U-shaped staple is attached to an end of the plunger.

FIGS. 4A and 4B show another embodiment of staple assemblies in accordance with the invention, in which a staple, for example, the U-shaped staple 490 of FIG. 4B, is swagingly secured to distal end 410 of plunger 495. FIG. 4A illustrates plunger 495 in the configuration before attachment of U-shaped staple 490. Here, plunger 495 contains one or more projecting portions 420 that project substantially perpendicularly from a surface of distal end 410, which in the embodiment illustrated in FIG. 4A is substantially flat. Projecting portions 420 in FIG. 4A are arranged circumferentially around portion 430 of distal end 410, which is configured to receive the staple. In other aspects of this embodiment, any number of similar projecting portions may be present, each located either circumferentially within or around portion 430. Portion 430 may contain one or more grooves 435 as shown in FIG. 4A that are shaped to receive the staple; such a configuration may provide better slippage-free attachment of the staple to distal end 410. Further, as shown in the embodiment of FIG. 4A, distal end 410 may additionally include a retaining projecting portion 445 that is used for vertical retention of plunger 495.

FIG. 4B illustrates plunger 495 in a configuration in which U-shaped staple 490 has been swagingly secured to distal end 410. During the swaging process, projecting portions 420, which in this embodiment are made from plastic, are heated and swaged down to compress U-shaped staple 490 against the substantially flat surface of distal end 410 into a fixed configuration. Upon cooling of the swaged projecting portions 420, U-shaped staple 490 is fixed to distal end 410 as shown in FIG. 4B. Retaining projecting portion 445 of this embodiment is not swaged and remains in a projecting configuration, as depicted in FIG. 4B.

Figure 5A:
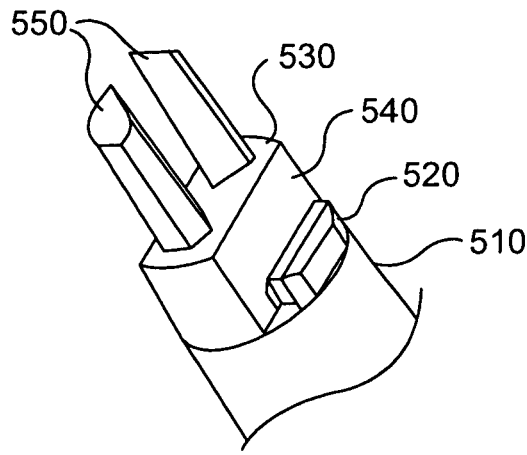
FIG. 5A is a view in perspective of a staple and plunger in accordance with yet another embodiment of the invention.
Figure 5B:
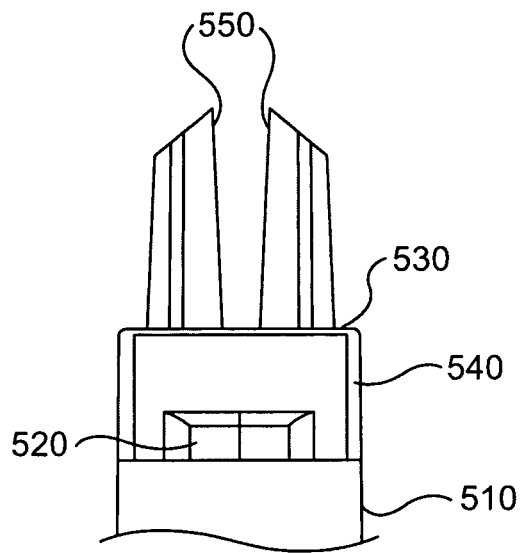
FIG. 5B is a side view of the staple and plunger of FIG. 5A.
Figure 5C:
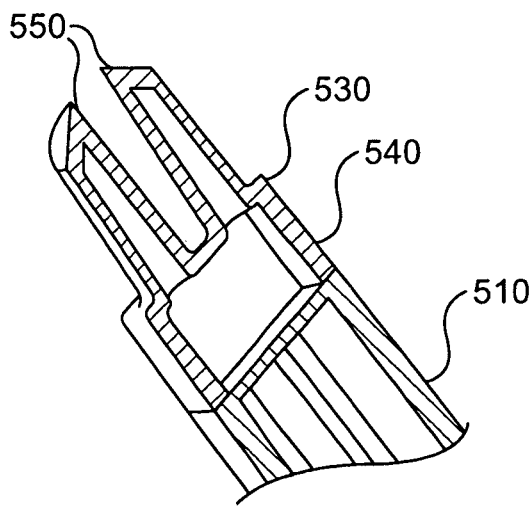
FIG. 5C is a cross-sectional view of the staple and plunger of FIG. 5A.

FIGS. 5A through 5F show another embodiment of a staple assembly in accordance with the invention in which the staple includes a thick base that is movably received within hooks projecting from the sides of the distal end of the plunger. FIG. 5A illustrates distal end 510, with staple 530 mounted thereon, in perspective, from a line of sight forming an obtuse angle with the axis of substantial symmetry of distal end 510. FIG. 5B shows the same configuration in profile, with the line of sight substantially perpendicular to that axis. FIG. 5C shows a cross section of the same configuration taken along a plane that is parallel to the axis of distal end 510. In this embodiment staple 530 comprises a thick base 540 and one or more tines 550 that provide the puncturing functionality. Distal end 510 includes projecting hooks 520 that project from distal end 510. In the embodiment shown in FIG. 5A, two such projecting hooks are present, each diametrically opposed to the other. These hooks provide rails through which corresponding flanges at the base of thick base 540 (not shown) are movably received; preferably, the combination is configured to provide friction-fitted engagement. Attachment of staple 530 to distal end 510 is provided in this way in the embodiment shown in FIGS. 5A-5C. Alternatively, securable attachment of staple 530 to distal end 510 may be provided by, for example, including a groove (or rib) at a predetermined location along the inner surface of projecting hook(s) 520, and a corresponding rib (or groove) on the surface of the flange(s) at the base of thick base 540 (not shown). Such a groove (or rib) on the inner surface of projecting hook(s) 520 corresponds to the rib (or groove) on the surface(s) of the flange at the base of thick base 540, allowing staple 530 to snap into a securably attached configuration within projecting hooks 520 of distal end 510. Other means for securably attaching staple 530 to distal end 510 will be apparent to those of skill in the art based on the present disclosure.

Figure 5D:
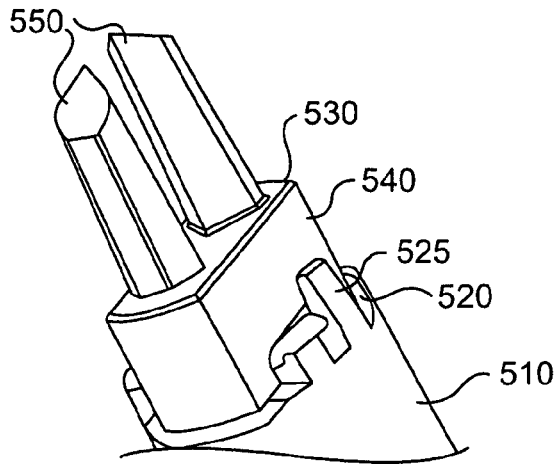
FIG. 5D is a view in perspective of an alternate embodiment of the staple and plunger of FIG. 5A.

FIG. 5D shows another version of the thick-based staple embodiment of FIGS. 5A-5C. In this embodiment, projecting hooks 520 of distal end 510 include a perpendicular member 525 that provides support and a greater compressive force for increasing the effectiveness of the friction-fitting engagement of projecting hooks 520 with the corresponding flanges at the base of thick base 540. Perpendicular member 525 also increases the strength and durability of projecting hooks 520. In this embodiment, the extension of the perpendicular member 525 beyond the upper surface of projecting hooks 520 is for the purpose of interacting with an adjacent part (not shown) to limit the load and/or impulse applied directly to staple 530; any such load or impulse is transferred to perpendicular member 525, thereby limiting the stresses applied to projecting hooks 520 by staple 530. This increases the durability of the design of this embodiment.

Figure 5E:
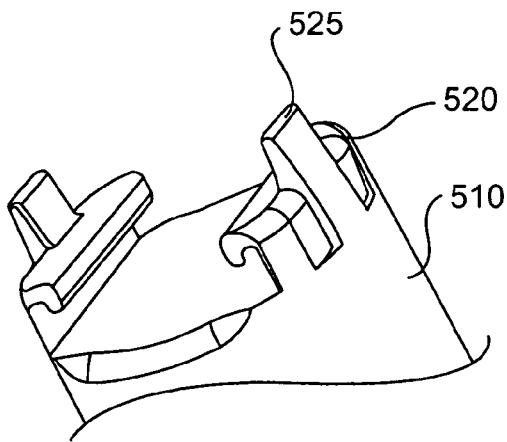
FIG. 5E is an enlarged view of the plunger of the embodiment of FIG. 5D without the staple.
Figure 5F:
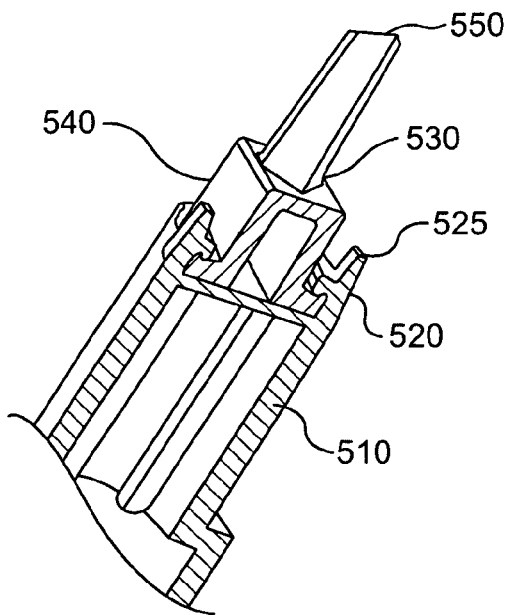
FIG. 5F is a cross-sectional view of an alternate embodiment of the plunger of FIG. 5D that has a staple assembly that includes a single tine.

FIG. 5E shows only distal end 510 (including projecting hooks 520 and perpendicular member 525) of the embodiment of FIG. 5D without staple 530 attached thereon. FIG. 5F shows an embodiment that is similar to the embodiment of FIGS. 5D and 5E in which only a single tine (tine 550) is present on staple 530.

Figure 6A:
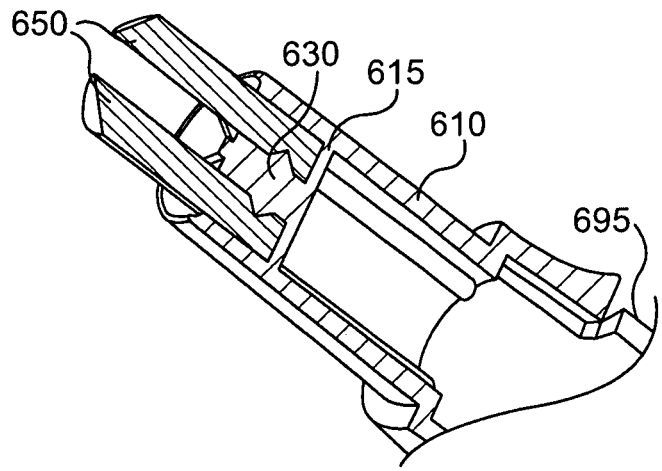
FIG. 6A is a cross-sectional view of another embodiment of a staple and plunger in accordance with the invention.
Figure 6B:
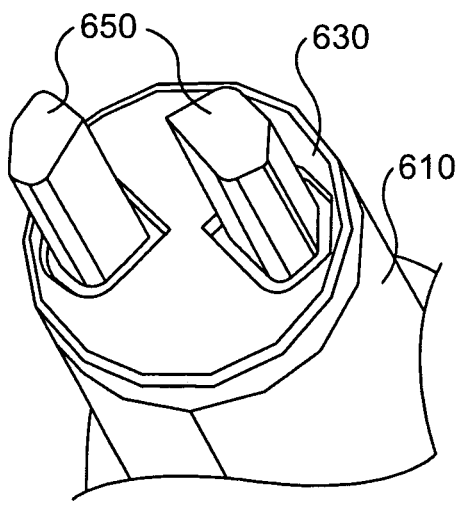
FIG. 6B is a view in perspective of the staple and plunger of the embodiment of FIG. 6A.
Figure 6C:
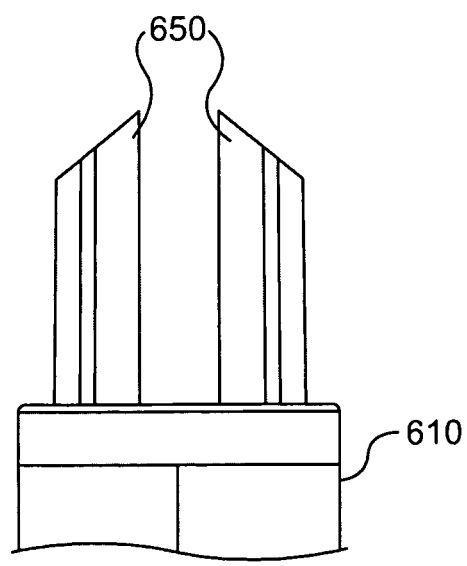
FIG. 6C is a side view of the staple and plunger of the embodiment of FIG. 6A.

FIGS. 6A-6C illustrate yet another embodiment of a staple assembly in accordance with the present invention in which one or more tines are insert molded onto the distal end of the plunger. FIG. 6A shows a cross section of plunger 695 of this embodiment, including distal end 610 and tines 650, taken along a plane that is parallel to the axis of substantial symmetry of plunger 695. In this embodiment, distal end 610 of plunger 695 has a cylindrical shape that provides a cylindrical volume 630 in which the bases of one or more tines 650 (i.e., prongs) are secured by injection molding of plastic within the cylindrical volume.

In this embodiment, the base of cylindrical volume 630 is bounded by a cylindrical plate 615, which provides separation of the injected-molded plastic within cylindrical volume 630 from the rest of the interior of distal end 610.

FIG. 6B illustrates the embodiment of FIG. 6A in perspective, from a line of sight that forms an obtuse angle with the axis of substantial symmetry of distal end 610. Similarly, FIG. 6C illustrates the same embodiment in profile, with the line of sight substantially perpendicular to the axis of distal end 510.

FIGS. 7C and 7D illustrate another embodiment of the present invention in which a cap is provided over the inhaler device of FIGS. 7A and 7B in a manner that prevents dust and grime from entering into the device. The cap additionally prevents inadvertent and unintentional operation of the device, which might occur when components of the device are subjected to random forces that trigger its operation without the volition of the user.

FIGS. 7A and 7B illustrate an inhaler device, for example, similar to the inhaler devices disclosed in U.S. Pat. Nos. 6,766,799 and 6,732,732. The inhaler device of FIGS. 7A and 7B comprises first casing portion 710 that is movably coupled to second casing portion 720. Second casing portion 720 comprises mouthpiece portion 725 and body portion 730. Body portion 730 includes vents 740 on its distal end, similar to and having the same functionality of vents 218 of FIG. 2. The inhalation device of FIGS. 7A and 7B may contain additional components, such as a staple assembly for puncturing and a capsule containing a dry-powder medicament, for example, as illustrated in FIG. 2, or in accordance with any other embodiment of staple assemblies of the invention. The inhaler device of FIGS. 7A and 7B is operated by compressing first casing portion 710 against second casing portion 720, which causes a staple attached to the spring-loaded plunger to pierce the capsule. The user may simultaneously or shortly thereafter inhale the dry-powder medicament through mouthpiece portion 725, which provides a path for flow for the medicament from the pierced capsule through vents 740 to the user's mouth.

FIGS. 7C and 7D illustrate a cap in accordance with one embodiment of the current invention for use with inhalers similar to the inhaler device of FIGS. 7A and 7B. Cap 750, as illustrated in FIG. 7D, may be placed on the inhaler device in a configuration in which it encloses second casing portion 720 and is securably attached to first casing portion 710. Cap 750 may be securably attached to first casing portion 710 in any way that will be apparent to one of ordinary skill in the art based on the present disclosure; for example, an approximately circular rib 755 (or groove) (see FIG. 7C) may be formed within the internal surface of cap 750 along the circumference of the intersection of a plane substantially perpendicular to the axis of substantial symmetry of cap 750 with cap 750. Similarly, a corresponding approximately circular groove (or rib) may be formed on the outer surface of first casing portion 710. Thus, cap 750 may be securably attached to first casing portion 710 by a snapping action, which causes the approximately circular rib 755 to move into place within the corresponding approximately circular groove.

When cap 750 is securably attached to first casing portion 710 as shown in FIG. 7D, the probability of dust and grime entering into the inhaler is reduced, because in this configuration cap 750 encloses mouthpiece portion 725 as well as body portion 730 of second casing portion 720. Further, because operation of the inhaler device is caused by pushing first casing portion 710 against second casing portion 720, and because the presence of cap 750 on the inhaler device in a securably attached configuration prevents or reduces relative motion of first casing portion 710 with respect to second casing portion 720, cap 750 in the securably attached configuration also prevents inadvertent operation of the inhaler device by the application of random forces to the device during periods when it is not in use.

Figure 8A:
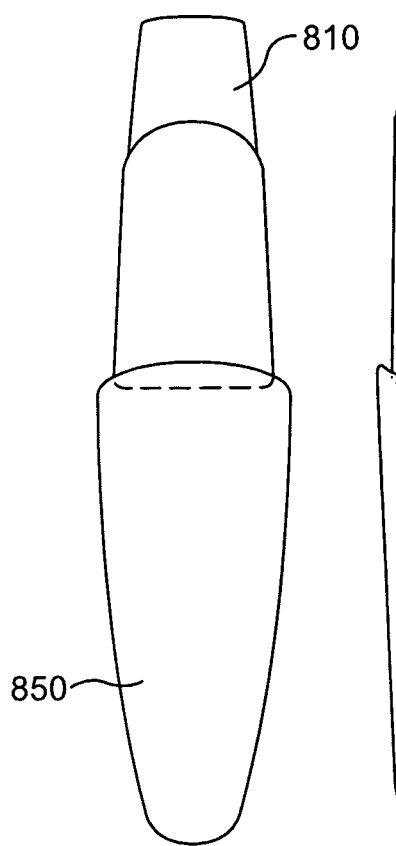
FIG. 8A is two side views of an alternate embodiment of the cap of FIG. 7C that is secured to an inhaler device.
Figure 8B:
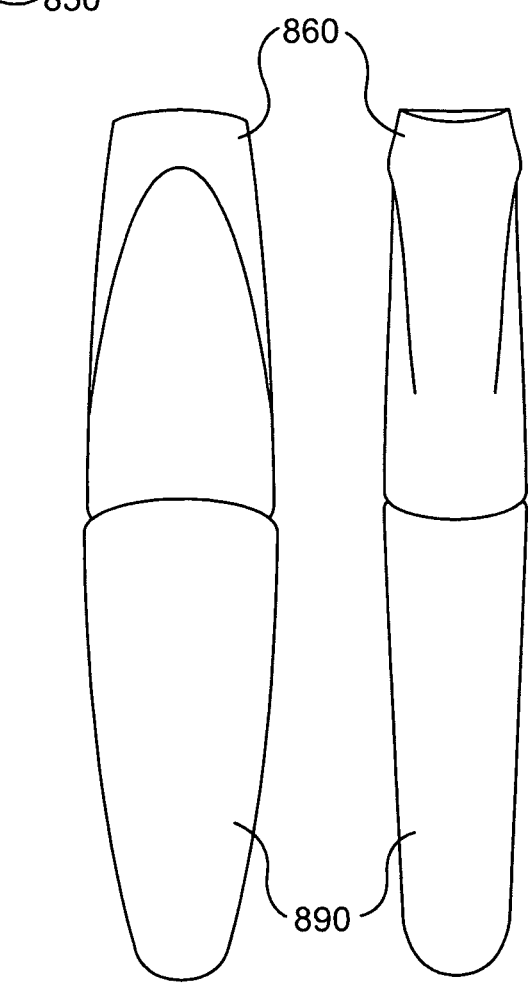
FIG. 8B is two side views of yet another alternate embodiment of the cap of FIG. 7C that is secured to an inhaler device.

FIGS. 8A and 8B depict other example embodiments of the cap of the present invention. The inhaler of FIG. 8A has a cap 850 that encloses all of the second casing portion (not shown) and that is coupled to first casing portion 810 in the inhaler device's closed position in a manner so that cap 850 only encloses a substantially small amount of the surface area of first casing portion 810. The inhaler of FIG. 8B has a cap 890 that encloses all of the second casing portion (not shown), and is coupled to first casing portion 860 in the inhaler device's closed position in a manner so that cap 890 substantially does not enclose any of the surface area of first casing portion 860. In this embodiment, when the inhaler device is in its closed position with cap 890 secured, the edges of the open end of cap 890 sit flush against the edges of the open end of first casing portion 860. Securable attachment of cap 890 to first casing portion 860 may be achieved through a snapping mechanism in this embodiment, for example, by placing a corresponding rib-groove pair along these edges of cap 890 and first casing portion 860.

Figure 9A:
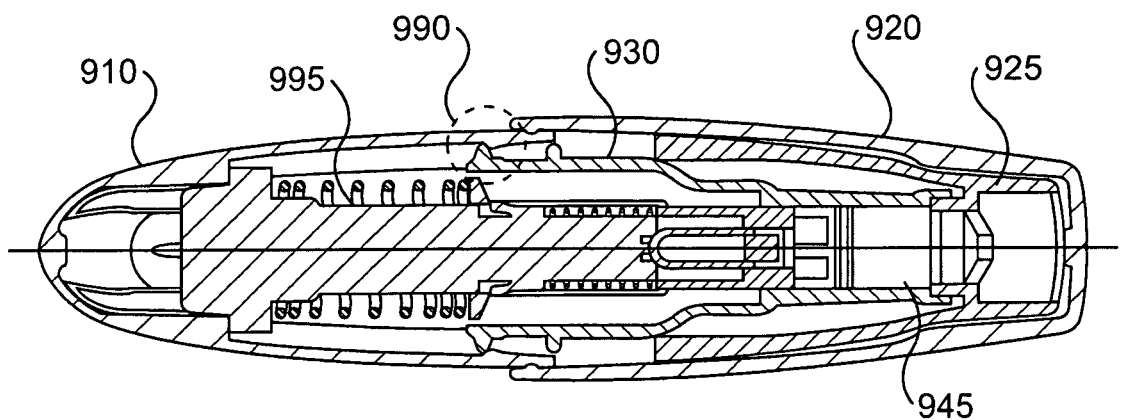
FIG. 9A is a view of an inhaler device in accordance with an embodiment of the invention in which the body portion and the first casing portion of the inhaler device are sealably coupled at a rest position of the device.
Figure 9B:
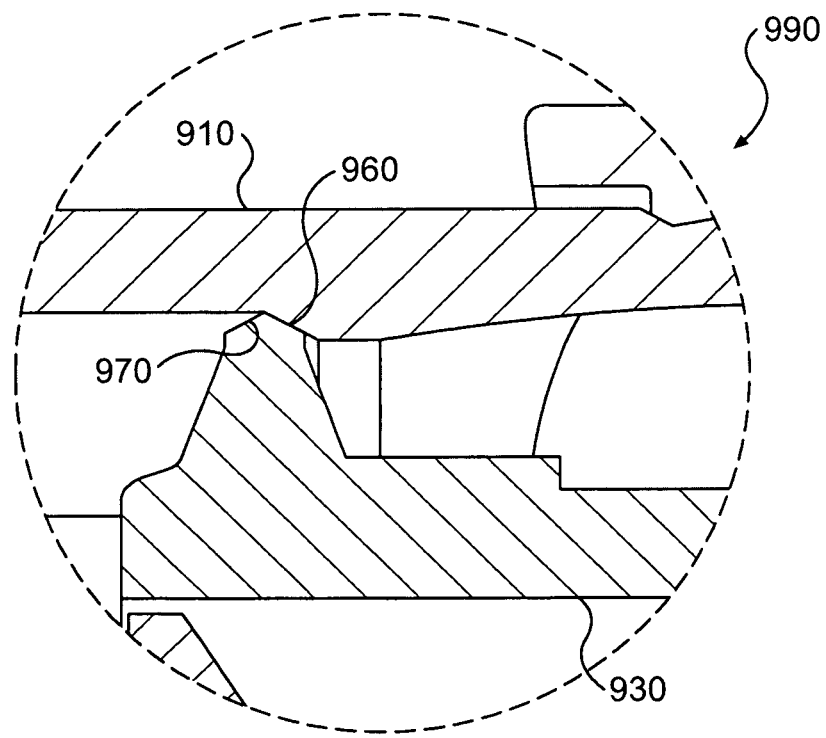
FIG. 9B is an enlarged view of the sealable coupling of FIG. 9A.

FIGS. 9A and 9B show another embodiment of the present invention that reduces undesired air flow into the inhaler device at its rest position by providing a substantially air-tight seal between the first casing portion and the body portion at that position. FIG. 9A illustrates, in cross-sectional profile, an inhaler device in accordance with this embodiment that is in its rest position. The inhaler device of FIG. 9A may, for example, have substantially similar components to the inhaler device of FIG. 2 (or an inhaler device in accordance with any other embodiment of the invention), such as first casing portion 910, second casing portion 920 (including mouthpiece portion 925 and body portion 930), plunger 995 and chamber 945. In this embodiment, corresponding structures at each of the distal ends of first casing portion 910 and body portion 930 are sealably coupled at the rest position of the inhaler device. Portion 990 of the inhaler device of FIG. 9A is shown in exploded view and greater detail in FIG. 9B. In this embodiment, body portion 930 at its distal end and outer surface has a radially projecting portion 970. The cross-section of the tip of radially projecting portion 970 forms a convex curve, as shown in FIG. 9B. The corresponding portion 960 of first casing portion 910 that is coupled to the tip of radially projecting portion 970 at the rest position of the inhaler device forms a concave curve, as shown in FIG. 9B.

The convex tip of projecting portion 970 and the corresponding portion 960 are shaped correspondingly so that they contact one another along a finite surface area of each. A substantially air-tight seal may result from the contact of such corresponding portions in such a manner; in particular, the biasing force of the springs in plunger 995 in the embodiment of FIGS. 9A and 9B causes these corresponding portions to push against one another, which results in a frictional seal.

Other embodiments for achieving such a substantially air-tight seal will be apparent to those with ordinary skill in the art based on the present disclosure. For example, in an embodiment that is the converse of the embodiment of FIGS. 9A and 9B, first casing portion 910 may have a projecting portion that forms, in cross section, a convex curve on at its distal end and on its inner surface, whereas body portion 930 at the corresponding position at its distal end and outer surface may form, in cross section, a corresponding concave curve. These components, which will be in contact at the rest position of the inhaler device of this embodiment, may once again form a substantially air-tight seal. In the embodiments of FIGS. 9A and 9B and its variations, the curves are preferably smooth curves, in that tangents to each curve are well-defined at all points along the curve. In other embodiments, the curves are smooth only along sections of contact of body portion 930 and first casing portion 910.

Figure 10A:
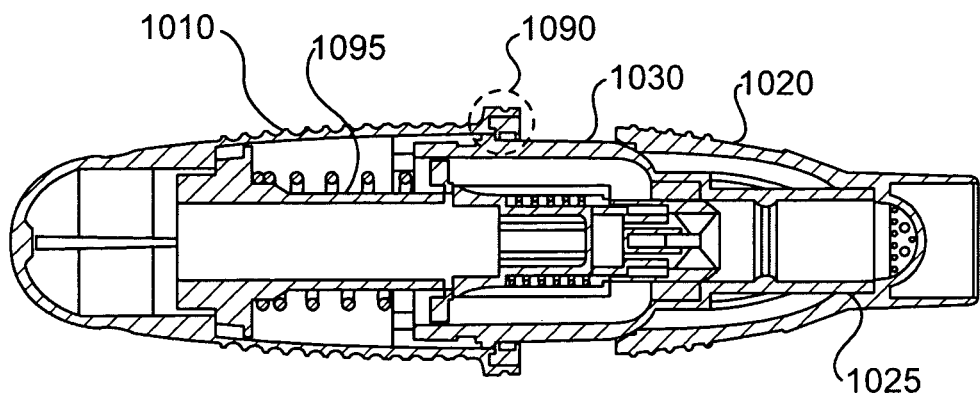
FIG. 10A is a view of an alternate embodiment of the invention in which the body portion and the first casing portion of the inhaler device are sealably coupled at a rest position of the device through an insert element.
Figure 10B:
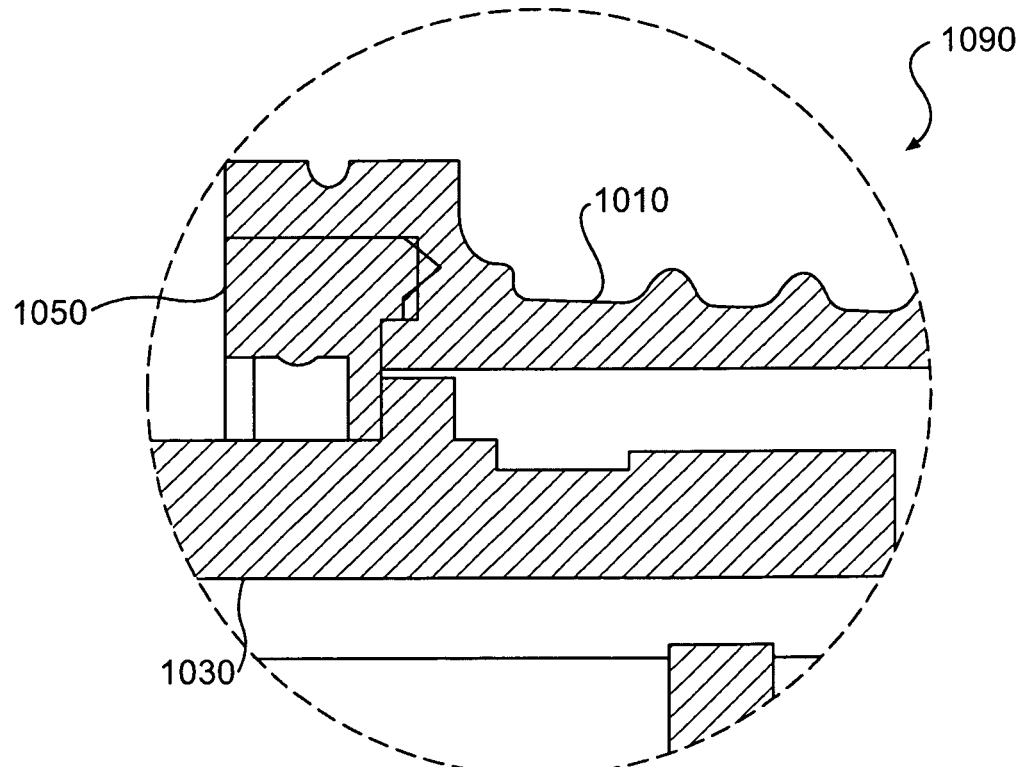
FIG. 10B is an enlarged view of the insert element of FIG. 10A.

FIGS. 10A and 10B illustrate another embodiment of the present invention for reducing undesired air flow into the inhaler device at its rest position by providing a substantially air-tight seal between the first casing portion and the body portion at the rest position. FIG. 10A shows an embodiment of the inhaler device of this embodiment at its rest position that has components substantially similar to those of the inhaler device of FIG. 2, such as first casing portion 1010, second casing portion 1020 (including mouthpiece portion 1025 and body portion 1030) and plunger 1095. The inhaler device of the embodiment of FIG. 10A additionally contains insert element 1050.

Portion 1090 of the inhaler device of FIG. 10A, including insert element 1050, is shown in exploded view and greater detail in FIG. 10B. Insert element 1050 is receivably and sealably coupled to the distal end of first casing portion 1010. For example, in a preferred embodiment, insert element 1050 is ultrasonically welded to the distal end of first casing portion 1010. Additionally, as shown in FIGS. 10A and 10B, insert element 1050 is sealably coupled to body portion 1030 at the rest position of the inhaler device. For example, the biasing force of the springs in plunger 1095 may cause a surface of insert element 1050 to push against a corresponding surface at the distal end of body portion 1030 at the rest position of the inhaler device, which results in a frictional seal. Such corresponding surfaces on insert element 1050 and the distal end of body portion 1030 are normal to the axis of the inhaler device in the embodiment illustrated in FIGS. 10A and 10B. Other embodiments will be apparent to those of skill in the art based on the present disclosure; for example, in an embodiment that is converse to the embodiment of FIGS. 10A and 10B, insert element 1050 may be receivably and sealably coupled to the distal end of the body portion. In this embodiment, insert element 1050 is also sealably coupled to the first casing portion at the rest position of the inhaler device.

While various embodiments of the present invention have been described above, it should be understood that they have been presented by way of example only, and not limitation. For example, the present invention is not limited to the physical arrangements or dimensions illustrated or described. Nor is the present invention limited to any particular design or materials of construction. As such, the breadth and scope of the present invention should not be limited to any of the above-described exemplary embodiments, but should be defined only in accordance with the following claims and their equivalents.

What is claimed is:

1. An inhalation device for administering a dose of powder contained in a receptacle, said device comprising:
   a first casing portion;
   a second casing portion movably coupled to said first casing portion, said second casing portion including a mouthpiece portion and a chamber configured to hold the receptacle;
   a plunger coupled to said first casing portion and movably coupled to said second casing portion, said plunger including a notched end;
   a hook member coupled to said plunger, and
   a substantially U-shaped staple coupled to said plunger, wherein the notched end and said hook member cooperatively secure the substantially U-shaped staple to the plunger.

2. The inhalation device of claim 1 wherein said substantially U-shaped staple is secured substantially parallel to an axis of said plunger.

3. The inhalation device of claim 1 wherein said hook member is fused to said plunger.

4. The inhalation device of claim 1 wherein said plunger further comprises at least one biasing spring, and wherein movement of said plunger with respect to said second casing portion is based on said at least one biasing spring.

* * * * *